United States Patent [19]

Kolar et al.

[11] 4,442,284
[45] Apr. 10, 1984

[54] CHEMICAL COMPOUNDS, AMINOACID ATTACHED TO GLYCOSIDE

[75] Inventors: Cenek Kolar, Marburg an der Lahn; Hans Paulsen, Hamburg, both of Fed. Rep. of Germany; Jean C. Jacquinet, Orléans-La Source, France

[73] Assignee: Behringwerke Aktiengesellschaft, Marburg an der Lahn, Fed. Rep. of Germany

[21] Appl. No.: 350,887

[22] Filed: Feb. 22, 1982

[30] Foreign Application Priority Data

Feb. 24, 1981 [DE] Fed. Rep. of Germany ....... 3106815

[51] Int. Cl.³ .............................................. C07H 15/04
[52] U.S. Cl. .................................. 536/17.9; 536/4.1; 536/53; 536/55; 260/112.5 R
[58] Field of Search ..................... 536/4.1, 17.9, 53, 55

[56] References Cited

U.S. PATENT DOCUMENTS 3,843,626 10/1974 Sutton .................................. 536/4.1
4,137,401 1/1979 Lemieux et al. ...................... 536/53
4,308,376 12/1981 Lemieux et al. ...................... 536/53

FOREIGN PATENT DOCUMENTS 53-96331 8/1978 Japan ...................................... 536/55

Primary Examiner—Johnnie R. Brown
Assistant Examiner—Elli Peselev
Attorney, Agent, or Firm—Curtis, Morris & Safford

[57] ABSTRACT

The text describes compounds having the formula I

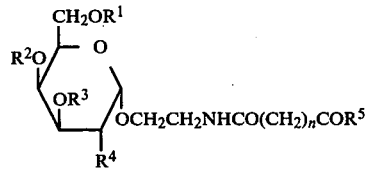

wherein $R^1$ denotes a hydrogen atom or an acyl or benzyl protective group, $R^1$ and $R^2$ together denote an alkylidene or benzylidene protective group, $R^2$ and $R^3$ denote hydrogen atoms or acyl or benzyl protective groups or a $\beta$-galactopyranosyl radical or a 2,3,4,6-tetra-0-acetylated derivative thereof, $R^4$ denotes an azido, amino or acetamido group, $R^5$ denotes —O—alkyl, —O—aryl, —O—benzyl, —NHNH$_2$, —N$_3$ or —OH and n denotes 1 to 10, and also a process for their preparation and their use as antigens or immunoadsorbents.

6 Claims, No Drawings

CHEMICAL COMPOUNDS, AMINOACID ATTACHED TO GLYCOSIDE

The invention relates to compounds of the general formula I

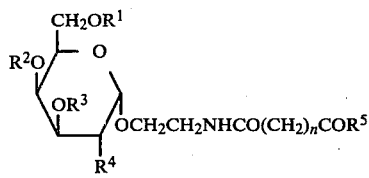

wherein $R^1$ denotes a hydrogen atom or an acyl or benzyl protective group, $R^1$ and $R^2$ together denote an alkylidene or benzylidene protective group, $R^2$ and $R^3$ denote hydrogen atoms or acyl or benzyl protective groups or a β-D-galactopyranosyl residue or the 2,3,4,6-tetra-O-acetylated derivative thereof, $R^4$ denotes an azido, amino or acetamido group, $R^5$ denotes —O—alkyl, —O—aryl, —O—benzyl, —NHNH$_2$, —N$_3$ or —OH and n denotes 1 to 10, a process for their preparation, and their use, attached to a carrier, as synthetic antigens or immunoadsorbents.

An antigen structure which is known as T-active antigen determinant can be exposed by the action of neuraminidase on red blood corpuscles.

This is the disaccharide derivative β-D-Gal(1→3)-D-GalNAc, which is attached by an alpha-glycoside linkage to a serine or threonine residue of a glycoprotein. It occurs in many glycoproteins and glycolipids.

This T-determinant is also found in tumor-associated antigens.

The preparation of synthetic antigens and immunoadsorbents which have a variety of uses and which have structural characteristics in the T-determinant requires chemical compounds which have these structural characteristics and which can be reacted with suitable carrier molecules.

It is known from German Offenlegungsschrift No. 2,630,596 that carbohydrates known to have hapten properties become synthetic antigens by being attached to a carrier via a spacer.

The object of the present invention is to prepare synthetic T-active antigens in which, as well as the carbohydrate part, the first amino acid attached by a glycoside linkage (serine or threonine) is also present as a structural unit.

This object is achieved by the preparation of compounds of the general formula I indicated.

Preferred compounds within the scope of the invention are those of the formula IV

α-D-GalNAc-OCH$_2$CH$_2$NHCO(CH$_2$)$_n$COOCH$_3$   IV of the formula V β-D-Gal(1-3)-α-D-GalNAc-
OCH$_2$CH$_2$NHCO(CH$_2$)$_n$COOCH$_3$   V of the formula VI

β-D-Gal(1-4)-α-D-GalNAc-
OCH$_2$CH$_2$NHCO(CH$_2$)$_n$COOCH$_3$   VI and of the formula VIII

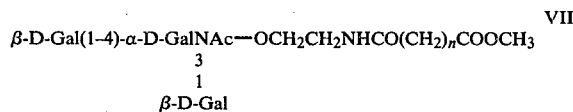

n being 4 or 7.

The process according to the invention for the preparation of the new compounds described above comprises (a) reacting a compound of the general formula VIII HOOC(CH$_2$)$_n$COR$^5$   VIII in which $R^5$ denotes O-alkyl, O-aryl or O-benzyl and n denotes 1 to 10, with 2-aminoethanol H$_2$N—CH$_2$—CH$_2$OH in a manner known per se to give the reaction product of the general formula III

HOCH$_2$CH$_2$NHCO(CH$_2$)$_n$COR$^5$   III (b) reacting the product from stage (a) in a manner known per se with a compound of the general formula II

in which $R^1$, $R^2$ and $R^3$ denote acyl groups, preferably acetyl or benzoyl groups, $R^4$ denotes —N$_3$ and Hal denotes Cl or Br, preferably to give an alpha-glycoside of the formula I, (c) converting the 2-azido group in the product from stage (b) in a manner known per se into the amino group, N-acetylating this group and splitting off the O-acetyl groups by means of alkali, the compound of the formula IV being thus formed, (d) converting the product of the formula IV from stage (c) in a manner known per se into a 4,6-O-alkylidene or 4,6-O-benzylidene compound of the general formula IX

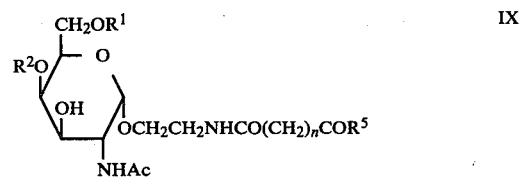

wherein $R^1$ and $R^2$ together denote the benzylidene group or an alkylidene group, (e) reacting the product of the formula IX from stage (d) in a manner known per se with a compound of the general formula X

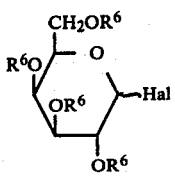

wherein $R^6$ is an acyl group, preferably acetyl or benzoyl, and Hal is Br or Cl, to give a disaccharide derivative, linked in the β-position, of the general formula XI

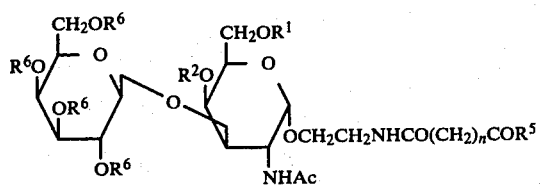

(f) subjecting the product of the formula XI from stage (e) in a manner known per se:

1. to hydrolysis with acids or hydrogenolysis with hydrogen in the presence of a catalyst, with elimination of the alkylidene or benzylidene protective groups, and
2. to alkaline treatment, whereby a compound of the formula V is formed, (g) treating the product of the formula XI from stage (e) in a manner known per se as under (f) 1. and protecting the free 6-OH group by means of an acyl group, preferably an acetyl or benzoyl group, whereby the compound of the general formula XII

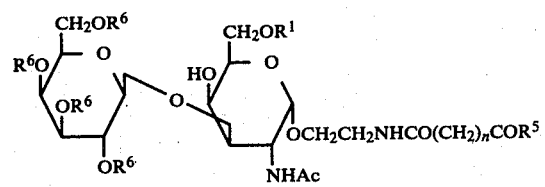

wherein $R^1$ and $R^6$ denote acyl, preferably acetyl or benzoyl, is formed, (h) reacting the product of the formula XII from stage (g) in a manner known per se as in stage (e) with the halide of the formula X to give a trisaccharide derivative and, after alkaline treatment, obtaining the trisaccharide compound of the formula VII which has a bridge-forming arm, (i) providing the 3-OH group of the N-acetyl-D-galactosamine unit in the product of the formula IX from stage (d) in a manner known per se with a protective group, preferably a benzyl, acetyl or benzoyl group, then splitting off the 4,6-O-benzylidene group by hydrolysis and finally protecting the 6-OH group selectively by means of a protective group, preferably an acetyl or benzoyl group, thereby obtaining a compound of the general formula XIII

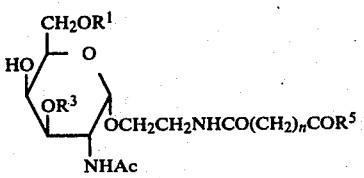

wherein $R^1$ denotes an acetyl or benzoyl group and $R^3$ denotes an acetyl, benzoyl or benzyl group, (j) reacting the product of the formula XIII from stage (i) in a manner known per se as in stages (e) and (h) with the halide of the formula X to give a disaccharide derivative and, after appropriately removing the protective groups, obtaining a compound of the formula VI, and (k) reacting the terminal carboxylic acid ester grouping of the bridge-forming arm in the products of the formulae IV to VII in a manner known per se so as to give $R^5$=OH, —NH—NH$_2$ or N$_3$.

The products from stage (k) can be attached in a manner known per se to soluble or insoluble carriers via their terminal amino groups, with the formation of an acid amide grouping.

Examples of such carriers are peptides and proteins, preferably human albumin or bovine serum albumin, white or red blood corpuscles, aminated plastics, aminated silica gel, plastics carrying amino groups, such as aminated polyacrylics, aminated polysaccharides, such as Sephadex, or lipids containing primary amino groups. When attached to carriers, the compounds of the formula I constitute the desired synthetic T-antigens.

SCHEDULE I

HOCH$_2$CH$_2$NHCO(CH$_2$)$_4$COOCH$_3$     Compound 1

HOCH$_2$CH$_2$NHCO(CH$_2$)$_7$COOCH$_3$     Compound 2

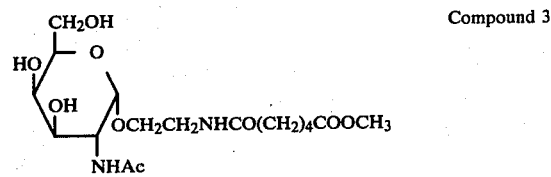

Compound 3

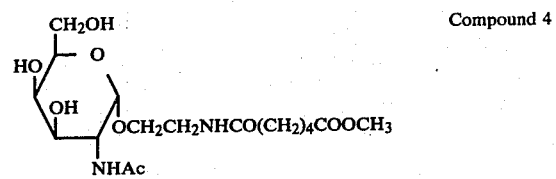

Compound 4

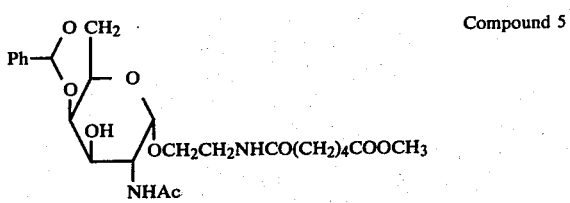

Compound 5

-continued
SCHEDULE I

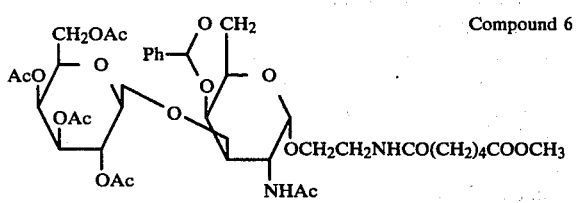
Compound 6

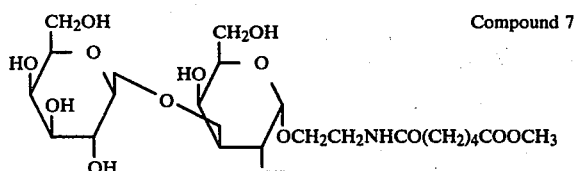
Compound 7

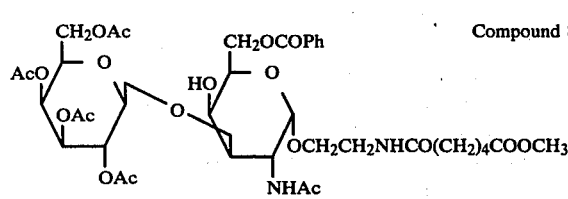
Compound 8

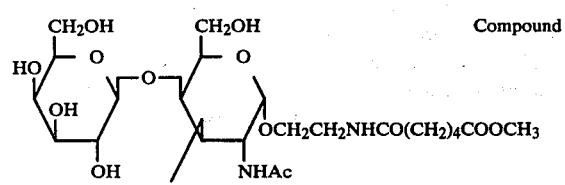
Compound 9

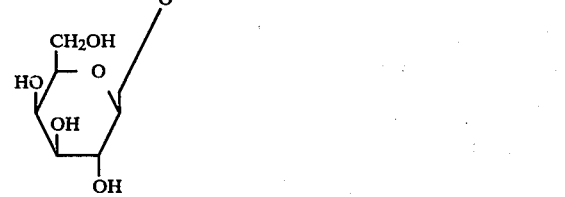
Compound 10
Bn = PhCH₂—

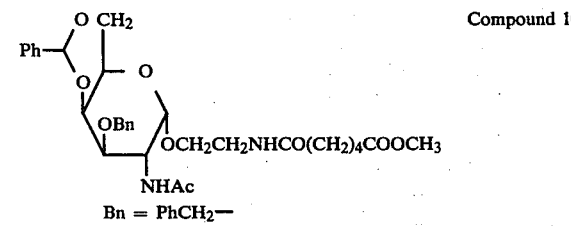
Compound 11
Bn = PhCH₂—

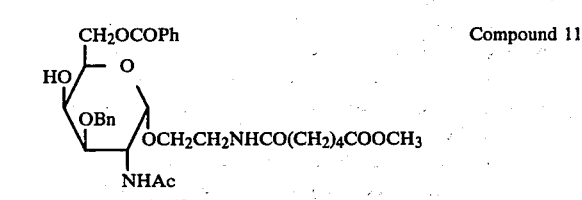

EXAMPLE 1

Preparation of
N-(5-methoxycarbonylvaleryl)-2-aminoethanol
(Compound 1)*

*The structural formulae of the most important compounds which are mentioned in the examples are shown specifically in Schedule I.

Method a 0.6 ml (10 mmoles) of 2-aminoethanol was added to 1.6 g (10 mmoles) of monomethyl adipate, dissolved in 20 ml of dry dimethylformamide (DMF), in the presence of 0.5 g of a dry molecular sieve having a pore width of 3 Å. After adding 2.06 g (10 mmoles) of dicyclohexylcarbodiimide, the suspension was stirred for 16 hours at room temperature. The mixture was filtered, the material on the filter was washed with chloroform and the filtrate was concentrated in vacuo. The crude product was purified by column chromatography (50 g of silica gel, migrating agent 10:1 $CH_2Cl_2/CH_3OH$).

Yield: 1.62 g (80%).

Method b 1.19 g (11 mmoles) of ethyl chloroformate were added at 0° C. to 2.02 g (10 mmoles) of monomethyl adipate, dissolved in 20 ml of dry tetrahydrofuran. 1.21 g (12 mmoles) of triethylamine were added dropwise while stirring. After stirring for one hour at room temperature, the mixture was filtered and the filtrate was concentrated in vacuo. The syrup obtained was dissolved in dry tetrahydrofuran (THF) and 1.8 ml (30 mmoles) of 2-aminoethanol were added at 0° C. After stirring for 16 hours at room temperature, the mixture was concentrated in vacuo and chloroform was added to the residue. The mixture was washed with water, dried over sodium sulfate and concentrated in vacuo. The crude product crystallized from cold diethyl ether.

Yield: 1.22 g (60%)

Melting point: 16° C.; $^1H$—NMR (270 MHz; $CDCl_3$)

Molecular weight: 203.24

EXAMPLE 2

Preparation of
N-(8-methoxycarbonylcapryl)-2-aminoethanol
(Compound 2)

Compound 2 was prepared from monomethyl azelaate and 2-aminoethanol in the same manner as that described in Example 1, Methods a and b.

Melting point: 56°–57° C.; $^1H$-NMR (100 MHz; $CDCl_3$)

Molecular weight: 245.32

EXAMPLE 3

N-(5″-Methoxycarbonylvaleryl)-2′-aminoethyl-2-acetamido-2-deoxy-alpha-D-galactopyranoside
(Compound 3)

2.03 g (10 mmoles) of 1 were dissolved in 80 ml of absolute nitromethane and 3.4 g (13 mmoles) of mercury-(II) cyanide and 0.34 g (0.94 mmole) of mercury-(II) bromide were added to the reaction mixture while stirring. 3.5 g (10 mmoles) of 3,4,6-tri-O-acetyl-2-azido-2-deoxy-β-D-galactopyranosyl chloride, dissolved in 30 ml of absolute nitromethane, were added dropwise in the course of 1 hour at room temperature and under an $N_2$ atmosphere. The mixture was stirred for 24 hours at room temperature. 200 ml of chloroform were added and the mixture was washed twice with saturated NaH- $CO_3$ solution and twice with saturated aqueous NaCl solution. The aqueous phases were extracted twice with $CH_2Cl_2$. The combined organic phases were dried with $Na_2SO_4$ and filtered and evaporated in vacuo. The crude product was dissolved in 40 ml of 1:1 glacial acetic acid/acetic anhydride, and 5 g of zinc powder were added while stirring. The solids were filtered off after 20 minutes and the filtrate was concentrated in vacuo. After being evaporated in vacuo several times, toluene being added each time, the syrup was dried for 2 hours in a high vacuum. The crude product was dissolved in 50 ml of absolute methanol and a 1 N solution of sodium methylate in methanol was added. After 24 hours the mixture was neutralized with Dowex 50 WX-8 (H⊕). The product was purified by column chromatography on 80 g of silica gel using 4:1 chloroform/methanol.

Yield: 1.62 g (40%).

The product crystallized from methanol/ether. Melting point: 206° C., $[alpha]_D^{20} = +104°$ (c=1, $H_2O$) $^1$H-NMR (270 MHz, DMSO-$d_6$): delta=4.57d (1-H $J_{1,2}=3.6$ Hz); 4.06 ddd (2-H, $J_{2,3}=11.0$ Hz, $J_{2,NH}=8.9$ Hz); 1.84 s (AcN); 3.56 s ($OCH_3$).

EXAMPLE 4

N-(8''-Methoxycarbonylcapryl)-2'-aminoethyl-alpha-acetamido-2-deoxy-alpha-D-galactopyranoside (Compound 4)

Compound 4 was prepared from 3,4,6-tri-O-acetyl-2-azido-2-deoxy-β-D-galactopyranosyl chloride and compound 2 in the same manner as in Example 3.

Melting point: 234° C.; $[alpha]_D^{20} = +89°$ C. (c=1, $H_2O$) $^1$H-NMR (270 MHz, DMSO-$d_6$).

EXAMPLE 5

N-(5''-Methoxycarbonylvaleryl)-2'-aminoethyl-2-acetamido-4,6-O-benzylidene-2-deoxy-alpha-D-galactopyranoside (Compound 5)

20 ml of freshly distilled benzaldehyde and 1.5 g of powdered zinc (II) chloride (previously fused to remove water) were added to 1.75 g (4.3 mmoles) of compound 3. The mixture was shaken for 24 hours and then poured into 60 ml of ice-cold, saturated aqueous $NaHCO_3$ solution. The mixture was extracted with chloroform and the organic phase was washed with water, dried with $Na_2SO_4$ and concentrated in vacuo. The crude product crystallized from hot ethanol.

Yield: 1.7 g (80%).

Melting point: 221° C.; $[alpha]_D^{20} = +110°$ (c=0.5 in 1:1 $CHCl_3/CH_3OH$). $^1$H-NMR (270 MHz, DMSO-$d_6$); delta=5.56 s (CHPh); 4.69 d (1-H, $J_{1,2}=3.4$ Hz); 4.07 ddd (2-H, $J_{2,3}=11.1$ Hz, $J_{2,NH}=8.5$ Hz); 3.79 m (3-H, $J_{3,4}=3.4$ Hz); 3.55 s ($OCH_3$) 1.25 s (NAc).

EXAMPLE 6

N-(5''-Methoxycarbonyl)-2'-aminoethyl-2-acetamido-3-O-(2,3,4,6-tetra-O-acetyl-β-D-galactopyranosyl)-4,6-O-benzylidene-2-deoxy-alpha-D-galactopyranoside (Compound 6).

0.49 g (1 mmole) of 5 was dissolved in 16 ml of 3:1 absolute nitromethane/benzene, and 0.51 g (2 mmoles) of mercury-(II) cyanide and 36 mg (0.1 mmole) of mercury-(II) bromide were added while stirring. 0.82 g (2 mmoles) of 2,3,4,6-tetra-O-acetyl-alpha-D-galactopyranosyl bromide, dissolved in 8 ml of benzene, was added dropwise in the course of 4 hours at 60° C. and under an $N_2$ atmosphere. After 16 hours the reaction mixture was filtered and the material on the filter was rinsed with $CH_2Cl_2$. The filtrate was washed twice with saturated aqueous $NaHCO_3$ solution and twice with saturated aqueous NaCl solution. The aqueous phases were extracted twice with $CH_2Cl_2$. The combined organic phases were dried with $Na_2SO_4$, filtered and evaporated in vacuo. The product was purified by column chromatography on 80 g of silica gel using 12:1 $CH_2Cl_2$/methanol.

Yield: 0.71 g (86%) of an amorphous product; $[alpha]_D^{20} = +81°$ (c=1, $CHCl_3$). $^1$H-NMR (270 MHz, $CDCl_3$) delta: 4.76 d (1'-H $J_{1',2'}=7.8$ Hz), 5.19 dd (2'-H $J_{2',3'}=10.4$ Hz), 2.14 m (4-OAcn.NAc).

EXAMPLE 7

N-(5''-Methoxycarbonylvaleryl)-2'-aminoethyl-2-acetamido-2-deoxy-3-O-(β-D-galactopyranosyl)-alpha-D-galactopyranoside (Compound 7).

650 mg (0.78 mmole) of 6 in 20 ml of 60% strength acetic acid were warmed at 80° C. for ½ hour. The solution was then evaporated in vacuo. The syrup was dissolved in 50 ml of $CHCl_3$ and the solution was washed with water, saturated $NaHCO_3$ solution and water. After drying and evaporation in vacuo, 585 mg of syrup were obtained. The crude product was dissolved in 15 ml of absolute methanol, 2 ml of 0.2 N $NaOCH_3$ were added and the mixture was allowed to stand at room temperature for 24 hours. It was neutralized with Amberlite IR 120 H+, filtered and evaporated in vacuo. The crystalline mass which remained was recrystallized from methanol.

Yield: 360 mg (80%);

Melting point: 191° C., $[alpha]_D^{20} = +76.5°$ (c=1, $H_2O$) $^1$H-NMR (270 MHz, DMSO-$d_6$): delta=4.57 d (1-H $J_{1,2}=3.5$ Hz); 4.24 ddd (2-H $J_{2,3}=12.0$ Hz; $J_2$, NH=8.4 Hz); 4.3 d (1'-H $J_{1',2'}=7.3$ Hz); 1.84 s (NAc); 3.57 s ($OCH_3$).

EXAMPLE 8

N-(5''-Methoxycarbonylvaleryl)-2'-aminoethyl-2-acetamido-3-O-(2,3,4,6-tetra-O-acetyl-β-D-galactopyranosyl)-6-O-benzoyl-2-deoxy-alpha-D-galactopyranoside (Compound 8)

650 mg (0.78 mmole) of 6 in 60 ml of 60% strength acetic acid were warmed at 80° C. for ½ hour. The solution was then evaporated in vacuo and the resulting syrup was evaporated several times in vacuo, toluene being added each time, and the product was dried in a high vacuum. The product, $[alpha]_D^{20} = +51°$ (c=1, $CHCl_3$), was dissolved in 30 ml of $CH_2Cl_2$ and 15 ml of pyridine. 160 mg (1.3 mmoles) of benzoyl cyanide were added and the mixture was stirred for 7 hours at room temperature. 15 ml of methanol were then added and the mixture was concentrated to a syrup. The syrup was purified by column chromatography (60 g of silica gel; migrating agent 14:1 $CH_2Cl_2$/methanol).

Yield: 550 mg (83%).

Melting point: 171° C.; $[alpha]_D^{21} = +42°$ (c=1, 1:1 $CHCl_3$/methanol), $^1$H-NMR (270 MHz, $CDCl_3$) delta=7.45–7.58 m (Ph), 4.88 d (1-H $J_{1,2}=3.4$ Hz); 4.68 d (1'-H $J_{1',2'}=7.9$ Hz) 5.22 dd (2'-H $J_{2',3'}=10.4$ Hz); 5.01 dd (3'-H $J_{3',4'}=3.6$ Hz); 1.99 s; 2.02 s; 2.04 s; 2.10; 2.17 s (4 OAc+NAc).

EXAMPLE 9

N-(5″-Methoxycarbonylvaleryl)-2′-aminoethyl-2-acetamido-4-O-(β-D-galactopyranosyl)-3-O-(β-D-galactopyranosyl)-3-O-(β-D-galactopyranosyl)-alpha-D-galactopyranoside (Compound 9)

340 mg (0.4 mmole) of 8 were dissolved in 12 ml of 2:1 absolute nitromethane/benzene, and 260 mg (1 mmole) of mercury-(II) cyanide and 36 mg (0.01 mmole) of mercury-(II) bromide were added at 60° C. 320 mg (0.8 mmole) of 2,3,4,6-tetra-O-acetyl-alpha-D-galactopyranosyl bromide in 4 ml of benzene were added dropwise, while stirring. The mixture was worked up further as in Example 6. The product crystallized from ether/hexane. Yield: 360 mg (76%);

Melting point: 149° C.; [alpha]$_D^{20}$ = +22° (c=1 CHCl$_3$) $^1$H-NMR (270 MHz, CDCl$_3$): delta=4.75 d (1-H J$_{1,2}$=3.7 Hz) 4.69 d (1′-H J$_{1',2'}$=7.8 Hz); 5.05 d (1″-H J$_{1'',2''}$=7.8 Hz).

The peracetylated product was dissolved in 20 ml of methanol, and 2 ml of 0.2 N NaOCH$_3$ were added. After 24 hours the mixture was neutralized with Amberlite IR 120 H$^+$ and filtered and the filtrate was evaporated in vacuo. The product was dried over P$_2$O$_5$ in a high vacuum for several hours. Yield: 205 mg (92%) of an amorphous product; [alpha]$_D^{20}$ = +15.6° (c=1 H$_2$O).

EXAMPLE 10

N-(5″-Methoxycarbonylvaleryl)-2′-aminoethyl-2-acetamido-3-O-benzyl-4,6-O-benzylidene-2-deoxy-alpha-D-galactopyranoside (Compound 10).

495 mg (1 mmole) of 5 were dissolved in 25 ml of absolute DMF. After adding 1.38 g (9 mmoles) of BaO and 315 mg (1 mmole) of Ba(OH)$_2$.8H$_2$O, 0.6 ml (5 mmoles) of benzyl bromide was added. The mixture was stirred for 7 hours with exclusion of moisture and 3 ml of methanol were then added. The mixture was then filtered, the material on the filter was rinsed with plenty of chloroform and the filtrate was concentrated in vacuo. The product was purified by column chromatography (40 g of silica gel, migrating agent 12:1 CH$_2$Cl$_2$/methanol).

Yield: 456 mg (78%);

Melting point: 209° C.; [alpha]$_D^{20}$ = +125° (c=1 1:1 CHCl$_3$/CH$_3$OH) $^1$H-NMR (270 MHz, DMSO-d$_6$): delta=7.35 m (Ph) 5.62 s (PhC$\underline{H}$); 4.58 dd (PhC$\underline{H_2}$); 4.75 d (1-H J$_{1,2}$=3.2 Hz) 4.29 dd (2-H J$_{2,3}$=11.6 Hz); 3.82 dd (3-H J$_{3,4}$=3.0 Hz)

EXAMPLE 11

N-(5″-Methoxycarbonylvaleryl)-2′-aminoethyl-2-acetamido-6-O-benzoyl-3-O-benzyl-2-deoxy-alpha-D-galactopyranoside (Compound 11).

450 mg (0.77 mmole) of 10 in 20 ml of 60% strength acetic acid were warmed at 80° C. for 1 hour. The solution was then evaporated in vacuo, htoluene was added to the resulting syrup and the toluene was then removed by distillation in vacuo, this procedure being repeated several times, and the syrup was dried in a high vacuum. The crude product (378 mg) was processed further as in Example 8 without further purification.

The resulting syrup crystallized from ethanol.

Yield: 381 mg (83%);

Melting point: 211° C.; [alpha]$_D$ = +72° (c=1, 1:1 CHCl$_3$/CH$_3$OH). $^1$H-NMR (270 MHz, DMSO-d$_6$) delta: 4.62 d (1-H J$_{1,2}$=3.8 Hz); 4.34 ddd (2-H J$_{1,2}$ Hz, J$_2$,NH=8.6 Hz); 3.65 dd (3-H J$_{3,4}$=2.8 Hz).

EXAMPLE 12

N-(5″-Methoxycarbonylvaleryl)-2′-aminoethyl-2-acetamido-2-deoxy-4-O-(β-D-galactopyranosyl)-alpha-D-galactopyranoside (Compound 12).

300 mg (0.5 mmole) of 11 were dissolved in 18 ml of 2:1 absolute nitromethane/benzene, and 256 mg (1 mmole) of mercury-(II) cyanide and 36 mg (0.1 mmole) of mercury-(II) bromide were added at 60° C. 411 mg (1 mmole) of 2,3,4,6-tetra-O-acetyl-alpha-D-galactopyranosyl bromide in 4 ml of benzene were added dropwise, while stirring. The mixture was worked up further as in Example 6.

The crude product (340 mg) was dissolved in 15 ml of glacial acetic acid and was hydrogenated in the presence of 200 mg of 10% strength palladium-on-charcoal for 5 hours at room temperature. The mixture was diluted with 20 ml of chloroform and filtered, the material on the filter was rinsed and the filtrate was concentrated in vacuo. The residue was taken up in 30 ml of CHCl$_3$ and washed with saturated NaHCO$_3$ solution and water. The product was purified by column chromatography (60 g of silica gel; migrating agent 14:1 CH$_2$Cl$_2$/methanol).

Yield: 262 mg (86%);

Melting point: 151° C.; [alpha]$_D^{20}$ = +44° (c=1, 1:1 CHCl$_3$/CH$_3$OH), $^1$H-NMR (270 MHz, DMSO-d$_6$) delta=4.61 d (1-H J$_{1,2}$=3.6 Hz) 4.90 d (1′-H J$_{1'2'}$=8.6 Hz); 4.88 dd (2′-H J$_{2'3'}$=8.6 Hz); 1.84–2.11 s (5 OAc+NAc).

The product was dissolved in 30 ml of absolute methanol and 2 ml of 0.2 N NaOCH$_3$ were added. After standing for 24 hours, the mixture was neutralized with Amberlite IR 120 H$^+$ and was filtered and the filtrate was evaporated in vacuo. The crystalline mass which remained was recrystallized from methanol/ethanol.

Yield: 166 mg (87%); [alpha]$_D^{20}$ = +23° (c=1 H$_2$O).

We claim:

1. A compound of the formula

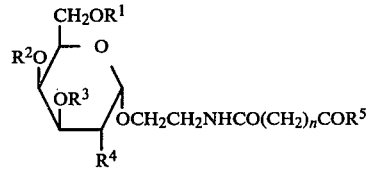

wherein R$^1$ taken alone is hydrogen, acetyl, benzoyl, or benzyl, R$^2$ and R$^3$ taken alone are hydrogen, acetyl, benzoyl, benzyl, beta-D-galactopyranosyl, or 2,3,4,6-tetra-O-acetylated beta-D-galactopyranosyl, R$^1$ and R$^2$ taken together are alkylidene or benzylidene, R$^4$ is azido, amino, or acetamido, R$^5$ is —OCH$_3$, —O—benzyl, —NHNH$_2$, —N$_3$, or —OH, and n is an integer from 1 to 10.

2. A compound as in claim 1 wherein R$^1$ is hydrogen, acetyl, or benzoyl, R$^1$ and R$^2$ taken together are isopropylidene or benzylidene, and R$^5$ is —OCH$_3$, —NHNH$_2$, —N$_3$, or —OH, and n is an integer from 4 to 7.

3. A compound as in claim 1 wherein R$^1$, R$^2$, and R$^3$ are hydrogen, R$^4$ is acetamido, and n is 4 or 7.

4. A compound as in claim 1 wherein R$^1$ is hydrogen, R$^2$ and R$^3$ are beta-D-galactopyranosyl, R$^4$ is acetamido, R$^5$ is —OCH$_3$, and n is 4.

5. A compound as in claim 1 wherein R$^1$ and R$^3$ are hydrogen, R$^2$ is beta-D-galactopyranosyl, R$^4$ is acetamido, R$^5$ is —OCH$_3$, and n is 4.

6. A compound as in claim 1 wherein R$^1$ and R$^2$ are hydrogen, R$^3$ is beta-D-galactopyranosyl, R$^5$ is —OCH$_3$, and n is 4.

* * * * *